(12) United States Patent
Ohori et al.

(10) Patent No.: US 7,820,593 B2
(45) Date of Patent: Oct. 26, 2010

(54) POWDERY PLANT VITALIZERS (75) Inventors: Koichi Ohori, Wakayama (JP); Hiroyuki Yamashita, Wakayama (JP); Tadayuki Suzuki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/487,898

(22) PCT Filed: Aug. 29, 2002

(86) PCT No.: PCT/JP02/08744

§ 371 (c)(1),
(2), (4) Date: Jun. 28, 2004

(87) PCT Pub. No.: WO03/017761

PCT Pub. Date: Mar. 6, 2003

(65) Prior Publication Data

US 2004/0235669 A1 Nov. 25, 2004

(30) Foreign Application Priority Data

Aug. 30, 2001 (JP) ............... 2001-261914
Jul. 30, 2002 (JP) ............... 2002-221446

(51) Int. Cl.
*A01N 25/02* (2006.01)
*A01N 25/00* (2006.01)
*A01N 25/04* (2006.01)
(52) U.S. Cl. .................... 504/116.1; 504/357
(58) Field of Classification Search .......... 504/116.1, 504/313, 314, 318, 351–353, 35, 116.17; 514/529, 546, 715, 717, 718, 720, 721, 724, 514/116.1, 313, 318, 351–353
See application file for complete search history.

(56) References Cited

U.S. PATENT DOCUMENTS 5,137,726 A   8/1992  Ogawa et al.
5,549,729 A * 8/1996  Yamashita ................. 71/26
6,489,269 B1* 12/2002 Hayashi et al. ............. 504/353
2001/0008635 A1* 7/2001  Quellet et al. .............. 424/408

FOREIGN PATENT DOCUMENTS

| EP | 0998850 A1 | 5/2000 |
| EP | 998850 A1 | 5/2000 |
| EP | 1114584 A1 | 7/2001 |
| EP | 1116515 A2 | 7/2001 |
| EP | 1151667 A2 | 11/2001 |
| EP | 1151668 A2 | 11/2001 |
| JP | 2000-198703 A | 7/2000 |

* cited by examiner

*Primary Examiner*—Jennifer M Kim
(74) *Attorney, Agent, or Firm*—Birch, Stewart, Kolasch & Birch, LLP (57) ABSTRACT

The present invention provides a powdery plant vitalizer and a powdery plant vitalizer composition which are resistant to the oozing of effective components and from which effective components are easily dispersed when the vertilizer is in contact with water to give vitality to plants. Specifically, the present invention relates to a powdery plant vitalizer containing a particle containing at least one compound (A) selected from a specific monohydric or dihydric alcohol (A1), a specific ether compound (A2), a specific fatty acid or its ester compound (A3), a specific organic acid derivative (A4) and a glycerin derivative (A5), an emulsifying-dispersing agent (B) and water-soluble sugars (C) or a particle containing the component (A) and water-soluble sugars (C') having an emulsifying and dispersing function, the particle having a structure in which the component (A) is dispersed in the form of an oil droplet in the particle, to a method of producing the powdery fertilizer and to a powdery plant fertilizer composition containing at least one selected from these powdery plant fertilizers and a fertilizer component.

5 Claims, 1 Drawing Sheet

POWDERY PLANT VITALIZERS

This application claims priority pursuant to 35 USC 119 based on Japanese patent application Nos. 2001-261914, filed Aug. 30, 2001, and 2002-221446, filed Jul. 20, 2002, as well as PCT application No. PCT/JP02/08744, filed Aug. 29, 2002.

FIELD OF THE INVENTION

The present invention relates to a powdery plant vitalizer which gives no chemical injury to plants and improves the vitality of plant bodies efficiently, and, particularly, to a powdery plant vitalizer which is easily emulsified and dispersed to develop plant vitalizing ability when it is in contact with water, to a method of producing the vitalizer and to a powdery plant vitalizer composition. It is to be noted that the plant vitalizer meant here means one which activates the whole of a plant, bringing about effects relating to the enhancement of plant growth such as the promotion of growth and improvement in yield.

PRIOR ART

Various nutrients are necessary for the growth of plants. It has been known that the shortage of some of these nutrients causes a hindrance to the growth of plants. For example, the shortage of nitrogen, phosphorous and potassium which are the three elements for fertilizer results in poor growth of plants in general.

These fertilizers are essential for the growth of plants. However, even if these fertilizers are supplied in a fixed amount or more, they cannot contribute to the growth of plants and to an improvement in yield beyond the level obtained by the fixed amount. However, it is an important problem concerning agricultural production to promote the growth of agricultural products and to increase the yield of agricultural products per unit area thereby increasing income. In this situation, plant growth regulators typified by gibberellin and auxin are used as materials or chemicals which affect specific physiological functions such as the elongation, flowering, fruiting, budding, rooting, abscission and defoliation of plants. However, the action of these materials is complicated and there is a possibility of these materials harming plants though depending on the method of use, with limiting of the use of these materials.

In order to solve such a problem, a plant vitalizer is disclosed in JP-A2000-198703 which includes a monohydric alcohol having 12 to 24 carbon atoms, gives no chemical injury to plants and improves the vitality of plant bodies efficiently. It is rather preferable to supply this plant vitalizer to plants in the form of an aqueous solution, an aqueous dispersion or an emulsion than to supply the primary alcohol having 12 to 24 carbon atoms to plants as it is upon use to make the vitalizer exhibit higher functions. In this case, the concentration of the primary alcohol is usually made to be 1 to 500 ppm.

The plant vitalizer in the above publication is preferably in the form of a powder, a granule, a tablet or the like and is desirably one which is made into a desired dispersion solution when dissolved upon use taking handling characteristics, preserving stability and the like into account.

Particularly, a powder is a preferable form because not only it is a commercial product as it is but also it may be used as raw material of a granule or tablet. Examples of the characteristics required for the powder include, besides solubility/dispersibility, a resistance to the oozing of effective components. When effective components are easily oozed, the powder is blocked during storing, leading to deteriorated solubility and there are many cases where molding processing (granulation and tabletting) becomes difficult.

DISCLOSURE OF THE INVENTION

Accordingly, the present invention relates to a powdery plant vitalizer and a powdery plant vitalizer composition which are resistant to oozing of effective components and from which effective components are easily dispersed when the vertilizer is in contact with water to give vitality to plants. Further, the present invention provides a method in which the powdery plant vitalizer and the powdery plant vitalizer composition can be obtained with ease.

The present invention relates to a powdery plant vitalizer containing a particle containing at least one compound (A) (hereinafter referred to as a component (A)) selected from the following (A1) to (A5), an emulsifying/dispersing agent (B) (hereinafter referred to as a component (B)) and water-soluble sugars (C) (hereinafter referred to as a component (C)) and having a structure in which the component (A) is dispersed in the form of an oil droplet in the particle.

(A1) Compounds represented by the following formula (1-1):

wherein $R^{11}$ represents a hydrocarbon group having 10 to 22 carbon atoms, $R^{12}$ represents a hydrogen atom, a hydroxyl group or a hydrocarbon group having 1 to 24 carbon atoms and $R^{13}$ represents a hydrogen atom or a hydrocarbon group having 1 to 24 carbon atoms, wherein any two groups among $R^{11}$, $R^{12}$ and $R^{13}$ may be combined to form a ring.

(A2) Compounds represented by the following formula (2-1):

wherein $R^{21}$ represents a hydrocarbon group which has 12 to 24 carbon atoms and may have at least one hydroxyl group, $R^{22}$ represents a hydrogen atom or a hydrocarbon group which has 1 to 24 carbon atoms and may have at least one hydroxyl group, AO represents an oxyalkylene group having 2 to 4 carbon atoms and m is the average addition mole number of alkylene oxides and denotes a number from 0 to 5, provided that $R^{22}$ is not a hydrogen atom when m is 0.

(A3) Compounds represented by the following formula (3-1):

wherein $R^{31}$ represents a hydrocarbon group which has 11 to 29 carbon atoms and may have at least one hydroxyl group, $R^{32}$ represents a hydrogen atom or a hydrocarbon group which has 1 to 30 carbon atoms and may have at least one hydroxyl group, —$COR^{33}$ ($R^{33}$ represents a hydrocarbon group having 11 to 23 carbon atoms) or a counter ion, AO represents an oxyalkylene group having 2 to 4 carbon atoms, n is the average addition mole number of alkylene oxides and denotes a number from 0 to 5.

(A4) Organic acid derivatives provided with an organic acid having at least two functional groups wherein a group containing 1 to 30 carbon atoms is bound with at least one of the functional groups.

(A5) Glycerol Derivatives

The present invention also relates to a method of producing the powdery plant vitalizer of the present invention, the method including the steps of preparing an O/W emulsion containing the components (A), (B) and (C) and water and drying the emulsion.

Also, the present invention relates to a second powdery plant vitalizer containing a particle containing the component (A) and water-soluble sugars (C') (hereinafter referred to as a component (C')) having an emulsifying-dispersing function and having a structure in which the component (A) is dispersed in the form of an oil droplet in the particle.

The present invention also relates to a method of producing the second powdery plant vitalizer of the present invention, the method including the steps of preparing an O/W emulsion containing the components (A) and the component (C') and water and water and drying the emulsion.

Moreover, the present invention relates to a powdery plant vitalizer composition containing at least one selected from the powdery plant vitalizer and second powdery plant vitalizer of the present invention and a fertilizer component.

DETAILED DESCRIPTION OF THE INVENTION

Component (A)

In the present invention, the component (A) is an effective component of the plant vitalizer and at least one compound selected from the following components (A1) to (A5).

Component (A1)

In the formula (1-1), each hydrocarbon group of $R^{11}$, $R^{12}$ and $R^{13}$ may be saturated or unsaturated and is preferably saturated or may be any of a straight-chain type, branched chain type and cyclic type, is preferably a straight-chain type or branched chain type and particularly preferably a straight-chain type. Also, any two of $R^{11}$, $R^{12}$ and $R^{13}$ may be combined to form a ring. Further, the total carbon number of the hydrocarbon group is preferably an odd number though it may be an odd number or even number.

Also, the total carbon number of $R^{11}$, $R^{12}$ and $R^{13}$ is preferably 50 or less, more preferably 10 to 48, even more preferably 10 to 44, even more preferably 10 to 22, even more preferably 12 to 20.

In the formula (1-1), the number of carbons of $R^{11}$ is preferably 12 to 22, more preferably 12 to 20 and still more preferably 14 to 18. Also, the compound represented by the formula (1-1) has a total carbon number of, preferably 12 to 48, more preferably 16 to 28 and particularly preferably 16 to 20. Further, the compound is preferably one having the total carbon number of 12 to 24 and one hydroxyl group, more preferably one having the total carbon number of 14 to 22 and one hydroxyl group and even more preferably one having the total carbon number of 16 to 20 and one hydroxyl group. Specific examples of the compound represented by the formula (1-1) include the following compounds.

(A1-1)

Examples of the compound represented by the formula (1-1) include 1-alkanols represented by $CH_3(CH_2)_{o-1}OH$ (o denotes an integer from 12 to 24, preferably 14 to 24, more preferably 14 to 22 and particularly preferably 16 to 20). Specifically, examples of the compound represented by the formula (1-1) include monohydric alcohols having 12 to 24 carbon atoms. Specific examples of the compound include 1-dodecanol, 1-tridecanol, 1-tetradecanol, 1-pentadecanol, 1-hexadecanol, 1-heptadecanol, 1-octadecanol, 1-nonadecanol, 1-eicosanol, 1-heneicosanol, 1-docosanol, 1-tricosanol and 1-tetracosanol.

(A1-2)

Examples of the compound represented by the formula (1-1) include 2-alkanols represented by $CH_3CH(OH)(CH_2)_{p-3}CH_3$ (p denotes an integer from 12 to 24, preferably 16 to 24 and more preferably 16 to 20). Specific examples of these 2-alkanols include 2-dodecanol, 2-tridecanol, 2-tetradecanol, 2-pentadecanol, 2-hexadecanol, 2-heptadecanol, 2-octadecanol, 2-nonadecanol and 2-eicosanol.

(A1-3)

Examples of the compound represented by the formula (1-1) include terminal unsaturated alcohols represented by $CH_2=CH(CH_2)_{q-2}OH$ (q denotes an integer from 12 to 24, preferably 16 to 24 and more preferably 16 to 20). Specific examples of these alcohols include 11-dodecene-1-ol, 12-tridecene-1-ol and 15-hexadecene-1-ol.

(A1-4)

Examples of other unsaturated long-chain alcohols include oleyl alcohol, elaidyl alcohol, linoleyl alcohol, linolenyl alcohol, eleostearyl alcohol (αorβ), ricinoyl alcohol and phytol.

(A1-5)

Examples of the compound represented by the formula (1-1) include 1,2-diols represented by $HOCH_2CH(OH)(CH_2)_{r-2}H$ (r denotes an integer of 12 to 24, preferably 16 to 24 and more preferably 16 to 20). Specific examples of these 1,2-diols include 1,2-dodecanediol, 1,2-tetradecanediol, 1,2-hexadecanediol and 1,2-octadecanediol.

Among the above (A1-1) to (A1-5), (A1-1), (A1-2), (A1-4) and (A1-5) are preferable, (A1-1), (A1-2) and (A1-4) are more preferable, (A1-1) and (A1-4) are still more preferable and (A1-1) is particularly preferable.

Component (A2)

In the formula (2-1) of the component (A2), each hydrocarbon group of $R^{21}$ and $R^{22}$ may be saturated or unsaturated and is preferably saturated or may be any of a straight-chain type, branched chain type and cyclic type, is preferably a straight-chain type or branched chain type and particularly preferably a straight-chain type. Also, each hydrocarbon group of $R^{21}$ and $R^{22}$ may have at least one hydroxyl group. Also, the total numbers of carbons of $R^{21}$ and $R^{22}$ are respectively preferably 50 or less, more preferably 12 to 48 and particularly preferably 16 to 44. Also, the compound represented by the formula (2-1) has a total carbon number of preferably 12 to 48, more preferably 24 to 48 and particularly preferably 32 to 40. AO in the formula (2-1) is preferably one or more groups selected from an oxyethylene group, oxypropylene group and oxybutylene group. m AOs may be the same or different and may be either random or block. Specific examples of the compound represented by the formula (2-1) include the following compounds. Among these compounds, compounds of the formula (A2-1) are preferable.

(A2-1)

Examples of the compound represented by the formula (2-1) include di-n-alkyl ethers represented by $CH_3(CH_2)_{s-1}$—O—$(CH_2)_{s-1}CH_3$ (s denotes an integer of 12 to 24, preferably 16 to 24 and more preferably 16 to 20) Specific examples of these di-n-alkyl ethers include didodecyl ether, ditridecyl ether, ditetradecyl ether, dipentadecyl ether, dihexadecyl ether and dioctadecyl ether.

(A2-2)

Examples of the compound represented by the formula (2-1) include vinyl ethers represented by $CH_2=CH-OR^{3a}$ ($R^{3a}$ represents an alkyl or alkenyl group having 12 to 24 and preferably 16 to 24 carbon atoms). Specific examples of these vinyl ethers include vinyl lauryl ether, vinyl myristyl ether, vinyl cetyl ether, vinyl stearyl ether, vinyl oleyl ether and vinyl linoleyl ether.

When the compound of the formula (2-1) has a hydrophilic group and a hydrophobic group, the Griffin's HLB of the compound is preferably less than 10, more preferably 8 or less, still more preferably 7 or less and particularly preferably 5 or less. This Griffin's equation is given by the following formula:

HLB=(Molecular weight of hydrophilic group/Molecular weight of surfactant)×(100/5) ("New Guide to Surfactant" Sanyo Chemical Industries, Ltd., issued on Nov. 1, 1985, p. 128).

Component (A3)

In the formula (3-1) of the component (A3), each hydrocarbon group of $R^{31}$ and $R^{32}$ may be saturated or unsaturated and is preferably saturated or may be any of a straight-chain type, branched chain type and cyclic type, is preferably a straight-chain type or branched chain type and particularly preferably a straight-chain type. Also, the total numbers of carbons of $R^{31}$ and $R^{32}$ are respectively preferably 50 or less, more preferably 12 to 48 and particularly preferably 16 to 44.

Also, the hydrocarbon group of $R^{31}$ may have at least one hydroxyl group. The number of carbons of the hydrocarbon group is preferably 11 to 29, more preferably 13 to 21 and still more preferably 15 to 19. Also, the hydrocarbon group of $R^{31}$ may be saturated or unsaturated and is preferably saturated or may be any of a straight-chain type, branched chain type and cyclic type, is preferably a straight-chain type or branched chain type and particularly preferably a straight-chain type. Specific examples of $R^{31}$ include alkyl groups such as a undecyl group, tridecyl group, pentadecyl group, heptadecyl group, nonadecyl group and heneicosyl group; and alkenyl groups such as a pentadecenyl group, heptadecenyl group and nonadecenyl group. Alkyl groups such as a pentadecyl group, heptadecyl group and nonadecyl group; and alkenyl groups such as a pentadecenyl group, heptadecenyl group and nonadecenyl group are more preferable. Alkyl groups such as a pentadecyl group, heptadecyl group and nonadecyl group are particularly preferable.

Also, $R^{32}$ in the formula (3-1) represents a hydrogen atom or a hydrocarbon group (preferably an alkyl group or an alkenyl group) which has 1 to 30 and preferably 1 to 22 carbon atoms and may have at least one hydroxyl group, —$COR^{33}$ ($R^{33}$ represents a hydrocarbon group having 11 to 23 carbon atoms) or a counter ion. Specific examples of $R^{32}$ include alkyl groups such as a lauryl group, tetradecyl group, hexadecyl group, octadecyl group, arachinyl group and behenyl group; acyl groups such as a lauroyl group, myristoyl group, palmitoyl group, stearoyl group, arachidoyl group and behenoyl group; and alkenyl groups such as a tetradecenyl group, hexadecenyl group, oleyl group, codoyl group and docosenyl group. Preferable examples include alkyl groups such as a hexadecyl group, octadecyl group and arachinyl group; acyl groups such as a palmitoyl group, stearoyl group and arachidoyl group; and alkenyl groups such as a hexadecenyl group, oleyl group and codoyl group. Particularly preferable examples include alkyl groups such as a hexadecyl group, octadecyl group and arachinyl group. As specific examples of the counter ion, any of alkali metals such as sodium and potassium, alkali earth metals such as calcium and magnesium, alkylamine salts such as trimethylamine and triethylamine and alkanolamine salts such as ethanolamine may be given. Among these examples, alkali metals and alkali earth metals are preferable.

AO in the formula (3-1) is preferably one or more groups selected from an oxyethylene group, oxypropylene group and oxybutylene group, wherein n AOs may be the same or different and may be any of a random type and block type.

Among the components (A3), compounds represented by the formula (3-1) wherein n is 0 to 5, $R^{31}$ is an alkyl group or an alkenyl group having 13 to 21 carbon atoms and $R^{32}$ is a hydrogen atom, an alkyl group having 1 to 22 carbon atoms or an acyl group, an alkenyl group having 2 to 22 carbon atoms or a counter ion (provided that the counter ion is excluded when n is not 0) are particularly preferable.

Also, when the compound of the formula (3-1) has a hydrophilic group and a hydrophobic group, the aforementioned Griffin's HLB is preferably less than 10, more preferably 8 or less, still more preferably 7 or less and particularly preferably 5 or less.

Component (A4)

Examples of the functional group of the component (A4) include a carboxyl group, hydroxyl group and amino group. The organic acid preferably has at least one hydroxyl group. Also, examples of the group to be connected to the functional group include an alkyl group, alkenyl group, alkylamino group and oxyalkylene group. As the component (A4), compounds represented by the following formula (4-1) are preferable.

$$A\text{-}(B)_n\text{—}C \quad (4\text{-}1)$$

wherein:

A and C: respectively represent a group selected from the following groups:

B: represents a group selected from the following groups:

X, Y and Z: respectively represent a hydrogen atom or a counter ion;

$R^{41}$, $R^{44}$ and $R^{49}$: respectively represent a hydrocarbon group having 1 to 30 carbon atoms;

$R^{45}$: a group selected from a hydrocarbon group having 1 to 30 carbon atoms and an acyl group having 1 to 30 carbon atoms.

$R^{42}$, $R^{43}$, $R^{46}$, $R^{47}$, $R^{48}$, $R^{4a}$, $R^{4b}$, $R^{4c}$, $R^{4d}$, $R^{4e}$ and $R^{4f}$: respectively represent a hydrogen atom or a hydrocarbon group having 1 to 30 carbon atoms;

a: a number of 0 or one or more;

l, m, n, o, p, q, r, s and t: respectively denotes a number of 0 to 10; and u and v: respectively denote a number of 1 to 50, wherein these groups and numbers are selected such that a group containing 1 to 30 carbon atoms is connected with at least one functional group in the molecule and B is not a group selected from when A and C are both groups selected from —$R^{44}$, —OH and —$OR^{45}$.

$R^{41}$, $R^{44}$ and $R^{49}$ in the formula (4-1) are respectively a hydrocarbon group having 1 to 30 carbon atoms. $R^{41}$ and $R^{49}$ are respectively a hydrocarbon group having preferably 12 to 26 and more preferably 14 to 22 carbon atoms. Also, $R^4$ is a hydrocarbon group having preferably 1 to 10 and more preferably 1 to 5 carbon atoms. $R^{41}$, $R^{44}$ and $R^{49}$ are respectively preferably an alkyl group or an alkenyl group. Also, the hydrocarbon group and preferably the alkyl group and alkenyl group of each of $R^{41}$, $R^{44}$ and $R^{49}$ may be either saturated or unsaturated and are preferably saturated, may be any of a straight-chain group, branched group and cyclic group, preferably a straight-chain group or branched group and more preferably a straight-chain group. Specific examples of $R^{41}$, $R^{44}$ or $R^{49}$ include alkyl groups such as a lauryl group, tetradecyl group, hexadecyl group, octadecyl group, eicosyl group (alkyl group having 20 carbon atoms), behenyl group (alkyl group having 22 carbon atoms); and alkenyl groups such as C14F1 group (the numeral next to C indicates the number of carbons and the numeral next to F indicates the number of unsaturated bonds, the same as follows), C16F1 group, C18F1 group, C20F1 group and C22F1 group.

$R^{42}$, $R^{43}$, $R^{46}$, $R^{47}$, $R^{48}$, $R^{4a}$, $R^{4b}$, $R^{4c}$, $R^{4d}$, $R^{4e}$ and $R^{4f}$ in the formula (4-1) respectively represent a hydrogen atom or a hydrocarbon group having 1 to 30, preferably 12 to 26 and more preferably 14 to 22 carbon atoms and preferably a hydrocarbon group. The hydrocarbon group is preferably an alkyl group or an alkenyl group. The hydrocarbon group and preferably the alkyl group or alkenyl group may be saturated or unsaturated and preferably saturated, and may also be any of a straight-chain group, branched group and cyclic group, preferably a straight-chain group or a branched group and more preferably a straight-chain group.

Also, X, Y and Z in the formula (4-1) are respectively a hydrogen atom or a counter ion. Specific examples of the counter ion include alkali metals such as sodium and potassium, alkali earth metals such as calcium and magnesium, alkylamine salts such as trimethylamine and triethylamine and alkanolamines such as ethanolamine. Alkali metals and alkali earth metals are preferable.

Also, a in the formula (4-1) is the total number of B. When two or more Bs in the formula (4-1) exist, that is, when a≧2, B may be the same or different types among the groups defined above.

The organic acid constituting the component (A4) is preferably hydroxycarboxylic acid such as citric acid, gluconic acid, malic acid, lactic acid and tartaric acid and more preferably citric acid.

When the component (A4) has a hydrophilic group and a hydrophobic group, the aforementioned Griffin's HLB of the component (A4) is preferably less than 10, more preferably 8 or less and particularly preferably 5 or less.

Component (A5)

The glycerin derivative of the component (A5) is preferably selected from the group consisting of esters of glycerin and an acid (hereinafter referred to as a glycerin ester), ethers of glycerin and a hydroxyl group-containing compound (hereinafter referred to as a glycerin ether), condensates of glycerin or their derivatives and glyceric acids and their derivatives.

The acids constituting glycerin esters may be either organic acids or inorganic acids. Examples of the organic acid include organic acids having 1 to 30, preferably 4 to 30 and more preferably 12 to 24 carbon atoms. Examples of the inorganic acid include phosphoric acid, sulfuric acid and carbonic acid and the inorganic ester may be a salt. As the glycerin ester, esters of glycerin and an organic acid, specifically, monoesters, diesters or triesters of glycerin and an organic acid are preferable. As the glycerin organic acid triester, synthesized triesters and oil & fats including animal oil & fats such as beef tallow, lard, fish oil and whale oil and vegetable oil & fats such as coconut oil, palm oil, palm stearin oil, caster oil, soybean oil and olive oil may be used, and oil & fats are preferable.

Examples of the hydroxyl group-containing compound constituting the glycerin ethers include alcohols having 1 to 30, preferably 4 to 30 and more preferably 12 to 24 carbon atoms. Examples of the glycerin ether include glycerin monoalkyl ethers such as butyl alcohol, isostearyl glyceryl ether and behenyl glyceryl ether. Diethers and triethers may also be used. Also, the glycerin ethers include alkylene oxide (hereinafter referred to as AO) adducts of glycerin. Here, the AO average addition mol number of the adduct is preferably 1 to 30, more preferably 1 to 10 and particularly preferably 1 to 5. Moreover, AO adducts of mixtures of oil & fats and glycerin may be used. The AO average addition mol number of the adduct is preferably 1 to 30, more preferably 1 to 10 and particularly preferably 1 to 5.

Examples of a glycerin condensate or its derivative include polyglycerins represented by the following formula (5-1) or their derivatives.

(5-1)

In the formula, n denotes a number of 2 to 50, R represents a hydrogen atom or an acyl group having 2 to 31 carbon atoms, X represents an alkylene group having 2 to 4 carbon atoms and $m_1$, $m_2$ and $m_3$ respectively denote a number of 0 to 3.

Glyceric acid is obtained by oxidizing glycerin or glyceryl aldehyde. In the present invention, glyceric acid derivatives such as glyceric acid esters and glyceric acid amides may be used.

It is to be noted that when the glycerin derivative according to the present invention has a hydrophilic group and a hydrophobic group, the aforementioned Griffin's HLB of the glycerin derivative is preferably less than 10, more preferably 8 or less and particularly preferably 5 or less.

Among the component (A) as aforementioned, monohydric alcohols having 12 to 24 carbon atoms are preferable, monohydric alcohols having 14 to 22 carbon atoms are more preferable and monohydric alcohols having 16 to 20 carbon atoms are even more preferable. The hydrocarbon group of the monohydric alcohol may be either saturated or unsaturated and may be any of a straight-chain type, branched type and cyclic type. The hydrocarbon group of the monohydric alcohol is preferably a straight-chain type or a branched type and particularly preferably a straight-chain alkyl group. Specific examples of the monohydric alcohol include 1-dodecanol (lauryl alcohol), 1-hexadecanol (cetyl alcohol), 1-octadecanol (stearyl alcohol), 1-eicosanol, 1-docosanol (behenyl alcohol), phytol and oleyl alcohol and alcohols derived from natural oil & fats.

These components (A) may be used in combinations of two or more according to the need.

The content of the component (A) in the powdery plant vitalizer is preferably 5% by weight or more and more preferably 10% by weight or more of the powdery plant vitalizer from an economical point of view. The content of the component (A) is preferably 70% by weight or less and more preferably 50% by weight or less of the powdery plant vitalizer from the viewpoint of solubility of the particle and the development of the effect of the particle. Accordingly, the content is preferably 5 to 70% weight and more preferably 10 to 50% by weight of the powdery plant vitalizer from the viewpoint of economy, solubility and the development of effects.

Component (B)

No particular limitation is imposed on the component (B) as far as it has the ability to emulsify and disperse the component (A) stably as oil droplets and gives no adverse influence in the stage of forming particles. Examples of the component (B) include nonionic surfactants such as sodium caseinate, gelatin, emulsion protein, water-soluble proteins such as soybean proteins, gums such as gum arabic and xanthane gum, cane sugar fatty acid ester, esterified processed starch, lecithin, glycerin fatty acid ester and polyglycerin fatty acid ester and anionic surfactants such as carboxylic acid types, sulfonic acid types, sulfate types and phosphate types.

It is to be noted that gums such as gum arabic and xanthane gum, esterified processed starch and the like may be used as the water-soluble sugars (C') component having emulsifying-dispersing ability.

It is preferable to use at least one emulsifying-dispersing agent having a solid state at normal temperature among these components from the viewpoint of the development of effects, emulsifying and dispersing ability and particle-forming ability. Specifically, a water-soluble protein and esterified processed starch are preferable and sodium caseinate and starch octenylsuccinate are particularly preferable.

Also, the aforementioned emulsifying-dispersing agents may be used in combinations of two or more. Combined effects can be expected by this combination.

The content of the component (B) in the powdery plant vitalizer is preferably 1% by weight and more preferably 5% by weight or more of the powdery plant vitalizer from the viewpoint of emulsifying-dispersing ability. The content of the component (B) is preferably 60% by weight or less, more preferably 50% by weight or less, even more preferably 40% by weight or less and even more preferably 30% by weight or less of the powdery plant vitalizer from the viewpoint of the development of effects, the solubility of particles and cost. Accordingly, the content of the component (B) is preferably 1 to 60% by weight, more preferably 1 to 50% by weight, even more preferably 5 to 40% by weight and even more preferably 5 to 30% by weight of the powdery plant vitalizer from the viewpoint of the development of effects, emulsifying-dispersing ability, solubility and cost.

Also, the ratio (B)/(A) by weight of the component (B) to the component (A) is preferably 1/5 to 5/1 and more preferably 1/3 to 3/1 with the view of developing the effects stably and obtaining a good solubility.

Component (C)

The component (C) is an excipient for fixing the component (A) as oil droplets to form particles and is water-soluble sugars which solve rapidly when they are in contact with water. Examples of these sugars include glucose, fructose, lactose, maltose, cane sugar, dextrin, cyclodextrin, maltose, fructose, pluran, or sugar alcohols such as sorbitol and mannitol. Among these sugars, dextrin is particularly preferable from the viewpoint of solubility, hygroscopicity and particle-forming ability. Also, the above water-soluble sugars may be used in combinations of two or more according to the need.

The content of the component (C) in the powdery plant vitalizer is preferably 5 to 90% by weight and more preferably 20 to 70% by weight of the powdery plant vitalizer from the viewpoint of particle-forming ability though no particular limitation is imposed on it because it is changed by the amounts of the components (A) and (B) to be compounded.

Water-soluble sugars (component (C')) having the ability to emulsify and disperse the component (A) in water may be used in place of the component (C). In this case, the component (B) may be either added or not. Specific examples of the component (C') include gums such as gum arabic, xanthane gum and esterified processed starch. The content of the component (C') in the powdery plant vitalizer is preferably 20 to 95% by weight and more preferably 30 to 85% by weight.

<Other Components>

The powdery plant vitalizer of the present invention may contain other materials according to the need besides the components (A), (B) and (C). Examples of these materials include an antioxidant, antiseptic, antistatic agent, chelating agent, breaking agent (water-soluble inorganic salts and water-insoluble materials) and fertilizer. The powdery plant vitalizer of the present invention may also contain the raw materials to be used and water derived from the production process. The content of water in the powdery plant vitalizer is preferably 10% by weight or less of the powdery plant vitalizer from the viewpoint of water activity relating to the proliferation of bacteria and more preferably 5% by weight or less from the viewpoint of suppressing blocking.

A surfactant may be further compounded separately with the intention of improving the dispersibility of the component (A) when the powdery plant vitalizer is dissolved in water. Preferable examples of the surfactant include ester group-containing nonionic surfactants, carboxylic acid type, sulfonic acid type, sulfate type and phosphate type anionic surfactants and amphoteric surfactants and sulfonic acid type surfactants and sulfate type surfactants are more preferable. These surfactants may be used in combinations of two or more.

<Powdery Plant Vitalizer>

The particle constituting the powdery plant vitalizer of the present invention has a structure in which the component (A) is dispersed in the state of oil droplets in the inside of a particle consisting of the components (B) and (C) or the component (C') according to the need.

Figure 1:
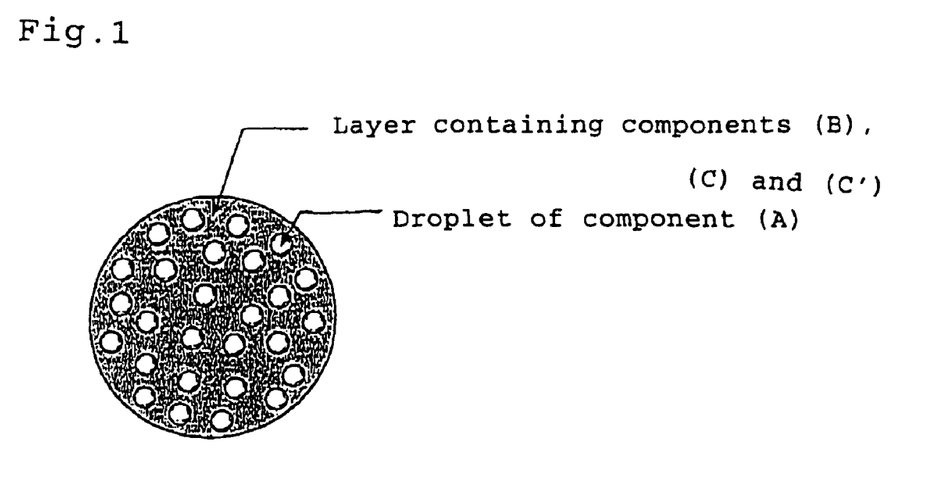
FIG. 1 is a schematic sectional view showing an example of a particle constituting a powdery plant vitalizer according to the present invention.
Figure 2:
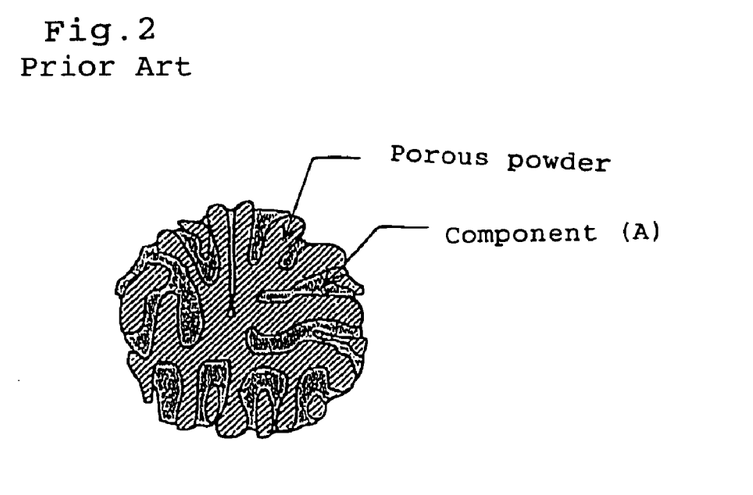
FIG. 2 (Prior Art) is a schematic sectional view showing an example of a porous powder to which a component (A) is absorbed or which is impregnated with a compound (A).

Here, the structure in which the component (A) is dispersed in the state of oil droplets in a particle implies the condition that the component (A) is present as small particles (oil droplets), the surface of which is covered by a layer consisting of the components (B) and (C) or the component (C') according to the need, so that the component (A) is discontinuously fixed. This condition should be discriminated from the condition that the component (A) is continuously retained when a particle is formed by allowing a porous body to adsorb (be impregnated with) the component (A). FIG. 1 shows an example of the structure of a particle according to the present invention and FIG. 2 shown an example of the structure obtained by allowing a porous body to adsorb (be impregnated with) the component (A).

The oil droplet of the component (A) may be either in a liquid state or in a solid state or may contain a part of other components. Also, the fixed state shows the condition of the component (A) retained in such a manner that it oozes out of the particle with difficulty. The oozing-out level of the component (A) is as follows if its is indicated in detail when the component (A) is fixed (so-meant in the present invention) inside of the particle: the component (A) is not oozed out at all at a power level applied by pressing strongly using fingers and the ooze rate is 5% by weight or less in a pressure test (see the measurement of ooze rate in the examples) using a copactor. On the other hand, in the case of the powder prepared by allowing a porous powder to adsorb (be impregnated with) the component (A), many ooze phenomena can be confirmed only by pressing using fingers and the ooze rate is 5% by weight or more in a pressure test using a copactor.

The particle constituting the powdery plant vitalizer has such a structure, which allows the components (B) and (C) and also the component (C') to dissolve when it is in contact with water and the component (A) is supplied as fine oil droplets or particles to plants to thereby be able to improve the vitality of these plants efficiently. Moreover, the particle is a powder which is limited in the ooze of the component (A) from the particle more greatly than the adsorption type (impregnated type) powder and therefore a number of merits such as limited blocking during storage, improved shape processability and an increase in the content of the component (A) can be obtained.

The structure in which the component (A) is dispersed in the form of an oil droplet may be identified by observing the sectional surface of the particle and by examining the dissolved and dispersed state of the powder and the ooze rate of the component (A) from the particle.

The average particle diameter of the particle constituting the powdery plant vitalizer of the present invention is preferably 10 to 500 μm and more preferably 20 to 300 μm from the viewpoint of solubility and fluidity. Also, the particle may be either a single particle or a coagulated particle.

Also, the average particle diameter of the component (A) dispersed in the form of an oil droplet in the particle constituting the powdery plant vitalizer of the present invention is preferably 50 μm or less, more preferably 0.05 to 50 μm and still more preferably 0.1 to 30 μm from the viewpoint of the effect of improving the vitality of plants. The average particle diameter of the component (A) dispersed in the form of an oil droplet can be measured by a laser diffraction/scattering method after the powdery plant vitalizer is dispersed in a liquid, such as water, which does not dissolve the component (A) (see a method of measuring emulsion-dispersion diameter in the examples).

As mentioned above, the powdery plant vitalizer of the present invention is a very effective powdery plant vitalizer which is dissolved and dispersed rapidly when it is in contact with water and can improve the vitality of plants efficiently when it is supplied to these plants. Here, the "plant vitalizer" activates the whole of the plant and has the effect of enhancing the growth of plants without any limitation to its use. Also, here the "plants" represent those recognized from the term "plant" itself and the plant on taxonomy such as vegetables, fruits, fruit trees, grains, seeds, bulbs, flowers and fragrant grasses (herbs).

The powdery plant vitalizer of the present invention as aforementioned is constituted of a particle containing the component (A) and the water-soluble sugars (component (C) or (C')), including a material having the ability of emulsifying and dispersing the component (A) in water and having a structure in which the component (A) is dispersed in the form an oil droplet in the particle.

<Method of Producing the powdery Plant Vitalizer>

As the method of producing the powdery plant vitalizer of the present invention, a method in which an O/W emulsion containing the components (A), (B) and (C) and water and dried is preferable although no particular limitation is imposed on the method as far as it is a method that can form a structure in which the component (A) is dispersed in the form of an oil droplet in the particle.

If the method in which the emulsion is dried is used, a capsule in which the surface of the component (A) is covered with a film constituted of the components (B) and (C) is formed, which permits the formation of a structure resistant to the oozing of the component (A), making it easy to obtain a powder having a high effect on restriction of blocking when the product is stored.

In the case of producing the particle constituting the powdery plant vitalizer by drying the emulsion, first the components (A), (B) and (C) and water are mixed to prepare an O/W emulsion (including a dispersion, the same as follows) to disperse the component (A) as fine droplets. At this time, it is preferable that the component (A) be used after it is melted under heating above the melting point of the component (A). The obtained O/W emulsion is dried by a usual drying method to obtain a particle in which the component (A) is dispersed in the form of an oil droplet.

It is to be noted that this also applies to the case where the component (C') is used in place of the components (B) and (C).

Although no particular limitation is imposed on the blending order of each component when the O/W emulsion is prepared, it is preferable, for example, that the components (B) and (C) be dissolved in water and the melted component (A) be added to the aqueous solution. Also, it is possible that the component (B) is dissolved in the component (A), which is then added to an aqueous solution of water and the component (C). The amount of water used at this time is preferably 20 to 300 parts by weight and more preferably 50 to 200 parts by weight based on 100 parts by weight of the constitutional components of the particle constituting the powdery plant vitalizer from an operational point of view though no particular limitation is imposed on the amount of water as far as a stable emulsion-dispersion solution can be formed.

Also, when emulsification-dispersion is carried out, it is preferable to use a an agitation type emulsifier such as a static type emulsifying-dispersing machine, homomixer or line mixer or a high pressure emulsifier such as a homogenizer to emulsify and disperse the component (A) stably into a desired size. If, particularly, the treatment is carried out using a high pressure emulsifier after a pre-dispersing operation is carried out using a static type emulsifying-dispersing machine or an agitation type emulsifier, a more uniform and finer emulsion-dispersion solution is obtained and is therefore preferable.

As to a method of drying the resulting O/W emulsion, a usual method may be used without any particular limitation. Examples of the drying method include a spray drying, freeze drying, vacuum drying, belt drying, tray drying and drum drying. When the emulsion is dried using a method other than the spray drying, it is then pulverized to obtain a particle having a desired particle diameter.

It is particularly preferable to use a spray drying method among the above drying methods from the viewpoint of industrial production and availability of a capsulated spherical particle.

When the particle constituting the powdery plant vitalizer is formed by a spray drying method, the particle diameter of the particle may be optionally adjusted by a spray nozzle to be used and, as required, the resulting particles are further coagulated to form a coagulated particle. Also, because the powdery plant vitalizer of the present invention is resistant to the oozing of components even if a load is applied, it may be made into a granule or tablet by extrusion granulation, briquetting and tablet-making.

Preferable examples of a combination of the components (A), (B) and (C) when the particle constituting the powdery plant vitalizer is produced by drying the emulsion include a combination of stearyl alcohol as the component (A), sodium caseinate or starch octenylsuccinate as the component (B) and dextrin as the component (C).

<Powdery Plant Vitalizer Composition>

The powdery plant vitalizer of the present invention may be made into a powdery plant vitalizer composition by further compounding a fertilizer component. In the case where a fertilizer component is sufficiently supplied as a base fertilizer in the soil when a powdery plant vitalizer is used, a satisfactory effect is obtained even if the powdery plant vitalizer is singly used. It is however preferable to compound a fertilizer component in the powdery plant vitalizer in such a culture form as to spray the fertilizer component by sprinkling to avoid excess use of the base fertilizer.

Examples of the fertilizer component used in the present invention include inorganic materials and organic materials which are supply sources of N, P, K, Ca, Mg, S, B, Fe, Mn, Cu, Zn, Mo, Cl, Si and Na, and particularly, N, P, K, Ca and Mg. Specific examples of the inorganic material include ammonium nitrate, potassium nitrate, ammonium sulfate, ammonium chloride, ammonium phosphate, sodium nitrate, urea, ammonium carbonate, potassium phosphate, calcium superphosphate, fused phosphate ($3MgO \cdot CaO \cdot P_2O_5 \cdot 3CaSiO_2$), potassium sulfate and magnesium carbonate. Also, examples of the organic materials include chicken droppings, cow dung, Bark compost, amino acid, peptone, mieki, fermented extract, calcium salts of organic acids (e.g., citric acid, gluconic acid and succinic acid) and calcium salts of fatty acids (formic acid, acetic acid, propionic acid, caprylic acid, capric acid and caproic acid).

The amount of these fertilizer components to be compounded is preferably 1 to 50000 parts by weight and more preferably 10 to 5000 parts by weight based on 100 parts by weight of the component (A).

The powdery plant vitalizer composition of the present invention may contain other components according to the need besides the fertilizer components. Examples of these other components include chelating agents, surfactants and diluents.

Examples of the chelating agent include polyvalent carboxylic acids such as citric acid, gluconic acid, malic acid, heptonic acid, oxalic acid, malonic acid, lactic acid, tartaric acid, succinic acid, fumaric acid, maleic acid, adipic acid and glutaric acid, potassium salts, sodium salts, alkanolamine salts or aliphatic amine salts of these carboxylic acids and aminocarboxylic acid type chelating agents such as EDTA, NTA and CDTA. These chelating agents may be used in combinations of two or more according to the need.

The amount of the chelating agent to be compounded is preferably 0 to 1000 parts by weight and more preferably 10 to 500 parts by weight based on 100 parts by weight of the component (A). The growth of plants can be promoted and fertilizer-absorbing efficiency can be improved by blending the chelating agent.

Examples of the surfactant include ester group-containing nonionic surfactants, anionic surfactants such as carboxylic acid types, sulfonic acid types, sulfates types and phosphate types and amphoteric surfactants: sulfonic acid type or sulfate type nonionic surfactants are preferable. These surfactants may be used in combinations of two or more according to the need.

The content of the surfactant in powdery plant vitalizer composition is preferably 0.05 to 10% by weight and more preferably 0.1 to 5% by weight. The dispersibility of the component (A) when the powdery plant vitalizer composition is dissolved in water can be improved by blending the surfactant.

As the diluent, water-soluble sugars (component (C)) which are an excipient for the powdery plant vitalizer may be used. Dextrin is particularly preferable from the viewpoint of solubility and hygroscopicity. The amount of the diluent to be compounded may be appropriately controlled in accordance with a final product without any particular limitation.

These fertilizer components and other components may be compounded either in the particle of the present invention or separately.

<Method of Producing the Powdery Plant Vitalizer Composition>

Although no particular limitation is imposed on the method of producing the powdery plant vitalizer composition of the present invention as far as it is a method of compounding a fertilizer component in the powdery plant vitalizer, the powdery plant vitalizer composition may be produced using, for example, the following methods.

1) A method in which a fertilizer component is compounded in the stage of preparing the O/W emulsion when the powdery plant vitalizer of the present invention is produced and then the O/W emulsion is dried by spraying to produce a powdery plant vitalizer composition.

2) A method in which the powdery plant viltalizer of the present invention is mixed with a fertilizer component.

As the mixer used when the powdery plant vitalizer is mixed with a fertilizer component, any mixer may be used without any particular limitation as far as it can mix the both sufficiently. Examples of the mixer include Nauter Mixer (manufactured by Hosokawamicron Corporation), V Blender (manufactured by (K.K) Dalton), High Speed Mixer (manufactured by Fukae Kogyo (K.K)), Henshel Mixer (manufactured by Mitsui Mining & Smelting Co., Ltd.), Redige Mixer (manufactured by Redige) and Ribbon Mixer (manufactured by Hosokawamicron Corporation).

The powdery plant vitalizer composition may be made into a granule or tablet by extrusion granulation, briquetting and tablet-making in the same manner as in the case of the powdery plant vitalizer.

The powdery plant vitalizer and powdery plant vitalizer composition of the present invention are easily emulsified and dispersed in contact with water and can improve the vitality of plants efficiently by supplying the emulsion-dispersion solution to the plants. Also, since the effective components scarcely ooze from the particle, these vitalizer and vitalizer composition have high effects on the restriction of blocking during storage, are easily granulated or made into a tablet and well keep up with the diversification of product forms.

EXAMPLES

Example 1

A 350 L stirring vessel equipped with a jacket and a dispersing blade (190 mmφ) was charged with 180 kg of ion exchange water and raised to 75° C. Then, 48 kg of dextrin (Pinedex #2, manufactured by Matsutani Chemical Industry Co., Ltd.) and 36 kg of esterified processed starch (Emalstar #30A, manufactured by Matsutani Chemical Industry Co., Ltd.) were added to the mixture with stirring the mixture to dissolve. 36 kg of melt stearyl alcohol (Kalcol 8098, manufactured by Kao Corporation) was added to the resulting aqueous solution and the mixture was subjected to an emulsifying operation. At this time, the stirring speed of the dispersing blade was maintained at 8 m/s and the temperature of the vessel was kept at 75 to 80° C.

Moreover, the above emulsion was processed by circulating it (elements: 5 pairs, processing flow rate: 2000 L/hr) using a static type emulsifying-dispersing machine (Bunsankun 15D manufactured by (K.K) Fujikin) to obtain an O/W type homogenized emulsion.

The obtained homogenized emulsion was spray-dried using a spray drier (AD-0506 N/R Model, Ashizawa•Niroatomizer (K.K)) in the following condition: the amount of the emulsion to be supplied: 40 kg/hr, blowing air temperature: 180° C. and the rotating speed of the atomizer: 4000 r/min (120 mmφ), to obtain a powdery plant vitalizer.

The resulting powdery plant vitalizer had an oil content (content of the component (A)) of 30.3% by weight and an average particle diameter of 230 μm. The particle did not allow the component (A) to ooze out even if a load was applied and was easily dissolved and dispersed when it was added in water to form an emulsion-dispersion solution having an average emulsion diameter of 0.5 μm. When this emulsion-dispersion solution was supplied to plants, it exhibited a high effect on an improvement in the vitality of the plants.

Example 2

The same stirring vessel that was used in Example 1 was charged with 100 kg of ion exchange water and raised to 75° C. Then, 66 kg of esterified processed starch (Emalstar #30A, manufactured by Matsutani Chemical Industry Co., Ltd.) was added to the mixture with stirring the mixture to dissolve. 34 kg of melt stearyl alcohol (Kalcol 8098, manufactured by Kao Corporation) was added to the resulting aqueous solution and the mixture was subjected to an emulsifying operation carried out in the following condition for about 1 hour: the stirring speed of the dispersing blade: 8 m/s and the temperature of the vessel: 75 to 80° C., to obtain an O/W type homogenized emulsion.

The obtained homogenized emulsion was spray-dried using the same spray drier that was used in Example 1 in the following condition: the amount of the emulsion to be supplied: 40 kg/hr, blowing air temperature: 200° C. and the rotating speed of the atomizer: 15000 r/min, to obtain a powdery plant vitalizer.

The resulting powdery plant vitalizer had an oil content (content of the component (A)) of 34.6% by weight and an average particle diameter of 146 μm. The particle did not allow the component (A) to ooze out even if a load was applied and was easily dissolved and dispersed when it was added in water to form an emulsion-dispersion solution having an average emulsion diameter of 1.3 μm. When this emulsion-dispersion solution was supplied to plants, it exhibited a high effect on an improvement in the vitality of the plants.

Example 3

The same stirring vessel that was used in Example 1 was charged with 150 kg of ion exchange water and raised to 75° C. Then, 20 kg of dextrin (Pinedex #2, manufactured by Matsutani Chemical Industry Co., Ltd.) and 40 kg of esterified processed starch (Emalstar #30A, manufactured by Matsutani Chemical Industry Co., Ltd.) were added to the mixture with stirring the mixture to dissolve. 40 kg of melt stearyl alcohol (Kalcol 8098, manufactured by Kao Corporation) was added to the resulting aqueous solution and the mixture was subjected to an emulsifying operation carried out in the following condition for about 1 hour: the stirring speed of the dispersing blade: 8 m/s and the temperature of the vessel: 75 to 80° C., to obtain an O/W type homogenized emulsion.

The obtained homogenized emulsion was spray-dried using the same spray drier that was used in Example 1 in the following condition: the amount of the emulsion to be supplied: 40 kg/hr, blowing air temperature: 200° C. and the rotating speed of the atomizer: 4,000 r/min, to obtain a powdery plant vitalizer.

The resulting powdery plant vitalizer had an oil content (content of the component (A)) of 40.7% by weight and an average particle diameter of 217 μm. The particle did not allow the component (A) to ooze out even if a load was applied and was easily dissolved and dispersed when it was added in water to form an emulsion-dispersion solution having an average emulsion diameter of 7.7 μm. When this emulsion-dispersion solution was supplied to plants, it exhibited a high effect on an improvement in the vitality of the plants.

Example 4

5 parts by weight of sodium caseinate (manufactured by Kishida Kagaku-sha) and 15 parts by weight of dextrin (Pinedex #2, manufactured by Matsutani Chemical Industry Co., Ltd.) were added to and mixed with in 60 parts by weight of water to dissolve.

20 parts by weight of melt stearyl alcohol (Kalcol 8098, manufactured by Kao Corporation) was gradually added to the resulting aqueous solution with stirring (10000 r/min) by a homomixer (manufactured by Tokushu Kika Kogyo Co., Ltd.) and the mixture was pre-emulsified for 20 minutes. At this time, the emulsion was kept at 70° C.

Next, the pre-emulsified emulsion was treated by a high-pressure homogenizer (manufactured by Nanomizer) at a primary pressure of 35 MPa to obtain an O/W type homogenized emulsion to be subjected to spray drying. The diameter of the resulting emulsion was about 3 μm.

The resulting homogenized emulsion was spray-dried using a spray drier (SD-1 Model, manufactured by Tokyo Rikakiki (K.K) in the following condition: the amount of the emulsion to be supplied: 220 g/hr, blowing air temperature: 100° C. and exhausting air temperature: 80° C., to obtain a powdery plant vitalizer.

The resulting powdery plant vitalizer had an oil content (content of the component (A)) of 20% by weight and an average particle diameter of 25 μm. The particle was easily dissolved and dispersed when it was added in water to form an emulsion-dispersion solution having an average emulsion diameter of about 3 μm. When this emulsion-dispersion solution was supplied to plants, it exhibited a high effect on an improvement in the vitality of the plants.

Example 5

A 10 L container was charged with 4.8 kg of water, to which were added 0.64 kg of sodium caseinate (manufactured by Kishida Kagaku-sha) and 1.92 kg of dextrin (Pinedex #2, manufactured by Matsutani Chemical Industry Co., Ltd.) under stirring using a homomixer (manufactured by Tokushu Kika Kogyo Co., Ltd.) and the mixture was raised to 75° C., followed by mixing and dissolving.

0.64 kg of melt stearyl alcohol (Kalcol 8098, manufactured by Kao Corporation) was gradually added to the resulting aqueous solution with stirring (10000 r/min) by a homomixer (manufactured by Tokushu Kika Kogyo Co., Ltd.) and the mixture was pre-emulsified for 40 minutes to obtain an O/W type homogenized emulsion. At this time, the emulsion was kept at 75° C. to 80° C.

The resulting homogenized emulsion was spray-dried using a spray drier (TRS-5W2N Model, manufactured by Sakamoto Giken) in the following condition: the amount of the emulsion to be supplied: 6 kg/hr and blowing air temperature: 140° C., to obtain a powdery plant vitalizer.

The resulting powdery plant vitalizer had an oil content (content of the component (A)) of 20.2% by weight and an average particle diameter of 31 μm. The particle did not allow the component (A) to ooze out even if a load was applied and was easily dissolved and dispersed when it was added in water to form an emulsion-dispersion solution having an average emulsion diameter of about 0.9 μm. When this emulsion-dispersion solution was supplied to plants, it exhibited a high effect on an improvement in the vitality of the plants.

Example 6

A 10 L container was charged with 4.8 kg of water, to which were then added 0.4 kg of sodium caseinate (manufactured by Kishida Kagaku-sha) and 1.2 kg of dextrin (Pinedex #2, manufactured by Matsutani Chemical Industry Co., Ltd.) under stirring using a homomixer (manufactured by Tokushu Kika Kogyo Co., Ltd.) and the mixture was raised to 75° C., followed by mixing and dissolving.

1.6 kg of melt stearyl alcohol (Kalcol 8098, manufactured by Kao Corporation) was gradually added to the resulting aqueous solution with stirring (10000 r/min) by a homomixer (manufactured by Tokushu Kika Kogyo Co., Ltd.) and the mixture was emulsified for 40 minutes. At this time, the emulsion was kept at 75° C. to 80° C.

Further, the above emulsion was treated using a high-pressure homogenizer (manufactured by Nanomizer) under a primary pressure of 35 MPa to obtain an O/W type homogenized emulsion.

The resulting homogenized emulsion was spray-dried in the same condition as in Example 5 to obtain a powdery plant vitalizer.

The resulting powdery plant vitalizer had an oil content (content of the component (A)) of 50.2% by weight and an average particle diameter of 35 μm. The particle did not allow the component (A) to ooze out even if a load was applied and was easily dissolved and dispersed when it was added in water to form an emulsion-dispersion solution having an average emulsion diameter of about 0.4 μm. When this emulsion-dispersion solution was supplied to plants, it exhibited a high effect on an improvement in the vitality of the plants.

Example 7

A 3 L container was charged with 1.2 kg of water, to which were added 0.12 kg of sodium caseinate (manufactured by Kishida Kagaku-sha), 0.04 kg of a sugar ester (DK Ester F-160, manufactured by Dai-ichi Kogyo Seiyaku Co., Ltd.) and 0.48 kg of dextrin (Pinedex #2, manufactured by Matsutani Chemical Industry Co., Ltd.) under stirring using a homomixer (manufactured by Tokushu Kika Kogyo Co., Ltd.) and the mixture was raised to 75° C., followed by mixing and dissolving.

0.16 kg of melt stearyl alcohol (Kalcol 8098, manufactured by Kao Corporation) was gradually added to the resulting aqueous solution with stirring (10000 r/min) by a homomixer (manufactured by Tokushu Kika Kogyo Co., Ltd.) and the mixture was emulsified for 20 minutes to obtain an O/W type homogenized emulsion. At this time, the emulsion was kept at 75° C. to 80° C.

The resulting homogenized emulsion was spray-dried using a spray drier (SD-1 Model, manufactured by Tokyo Rikaki (K.K) in the following condition: the amount of the emulsion to be supplied: 220 g/hr, blowing air temperature: 100° C. and exhausting air temperature: 80° C., to obtain a powdery plant vitalizer.

The resulting powdery plant vitalizer had an oil content (content of the component (A)) of 20.2% by weight and an average particle diameter of 13 μm. The particle did not allow the component (A) to ooze out even if a load was applied and was easily dissolved and dispersed when it was added in water to form an emulsion-dispersion solution having an average emulsion diameter of about 2.5 μm. When this emulsion-dispersion solution was supplied to plants, it exhibited a high effect on an improvement in the vitality of the plants.

Example 8

A 20 L Henshel mixer (manufactured by Mitsui Mining & Smelting Co., Ltd.) was charged with 2.52 kg of a water-soluble gardening fertilizer OKF2 (composition: N:P:K=14:8:16, manufactured by otsuka chemical Co., Ltd.), 0.2 kg of EDTA4Na (manufactured by Wako Pure Chemical Industries, Ltd.) and 0.08 kg of a sodium salt of a β-naphthalenesulfonic acid formalin condensate (trade name: Demol N, manufactured by Kao Corporation) and these components were mixed with stirring for 3 minutes. After the stirring was finished, 1.2 kg of the powder plant vitalizer obtained in Example 1 was further added to the mixture, which was then stirred for 1 minute to obtain 4.0 kg of a powdery plant vitalizer composition. The stirring speed was set to 9.4 m/s as a peripheral speed.

Example 9

A 20 L Henshel mixer (manufactured by Mitsui Mining & Smelting Co., Ltd.) was charged with 2.2 kg of a water-soluble gardening fertilizer OKF2 (composition: N:P:K=14:8:16, manufactured by Otsuka Chemical Co., Ltd.), 0.16 kg of 3Na citrate (manufactured by Wako Pure Chemical Industries, Ltd.), 0.02 kg of a sodium salt of a β-naphthalenesulfonic acid formalin condensate (trade name: Demol N, manufactured by Kao Corporation) and 0.02 kg of sodium laurylsulfate (trade name: Emal 10P) and these components were mixed with stirring for 3 minutes. After the stirring was finished, 1.6 kg of the powder plant vitalizer obtained in Example 1 was further added to the mixture, which was then stirred for 1 minute to obtain 4.0 kg of a powdery plant vitalizer composition. The stirring speed was set to 9.4 m/s as a peripheral speed.

Example 10

A 20 L Henshel mixer (manufactured by Mitsui Mining & Smelting Co., Ltd.) was charged with 1.5 kg of a water-soluble gardening fertilizer OKF2 (composition: N:P:K=14:8:16, manufactured by Otsuka Chemical Co., Ltd.), 0.1 kg of 3Na citrate (Wako Pure Chemical Industries, Ltd.), 0.02 kg of a sodium salt of a β-naphthalenesulfonic acid formalin condensate (trade name: Demol N, manufactured by Kao Corporation), 0.02 kg of sodium laurylsulfate (trade name: Emal 10P) and 1.56 kg of dextrin (Pinedex #2, manufactured by Matsutani Chemical Industry Co., Ltd.) and these components were mixed with stirring for 3 minutes. After the stirring was finished, 0.8 kg of the powder plant vitalizer obtained in Example 1 was further added to the mixture, which was then stirred for 1 minute to obtain 4.0 kg of a powdery plant vitalizer composition. The stirring speed was set to 9.4 m/s as a peripheral speed.

Example 11

A 20 L Henshel mixer (manufactured by Mitsui Mining & Smelting Co., Ltd.) was charged with 1.4 kg of a water-soluble gardening fertilizer OKF17 (composition: N:P:K=12:20:20, manufactured by Otsuka Chemical Co., Ltd.), 0.16 kg of succinic acid (Wako Pure Chemical Industries, Ltd.), 0.08 kg of sodium laurylsulfate (trade name: Emal 10P, manufactured by Kao Corporation) and 0.76 kg of dextrin (Pinedex #2, manufactured by Matsutani Chemical Industry Co., Ltd.) and these components were mixed with stirring for 3 minutes. After the stirring was finished, 1.6 kg of the powder plant vitalizer obtained in Example 1 was further added to the mixture, which was then stirred for 1 minute to obtain 4.0 kg of a powdery plant vitalizer composition. The stirring speed was set to 9.4 m/s as a peripheral speed.

Example 12

A 100 L Nauter Mixer (NX-1, manufactured by Hosokawamicron Corporation) was charged with 19.5 kg of dextrin (Pinedex #2, manufactured by Matsutani Chemical Industry Co., Ltd.), 10 kg of the powdery plant vitalizer obtained in Example 1, 1.25 kg of 3Na citrate (Wako Pure Chemical Industries, Ltd.), 0.25 kg of sodium salt of a β-naphthalenesulfonic acid formalin condensate (trade name: Demol N, manufactured by Kao Corporation), 0.25 kg of sodium laurylsulfate (Emal 10P, tradename of Kao Corporation) and 18.75 kg of a water-soluble gardening fertilizer OKF2 (composition: N:P:K=14:8:16, manufactured by Otsuka Chemical Co., Ltd.) and these components were mixed for 15 minutes in the following condition: rotation: 96 r/min and revolution: 3.3 r/min, to obtain 50 kg of a powdery plant vitalizer composition.

Comparative Example 1

Plants were grown only by water without compounding any plant vitalizer as a control when the effect of improving the vitality of plants was measured.

Comparative Example 2

A granule (Kalcol 8098, manufactured by Kao Corporation) which had an average particle diameter of about 1 mm and was constituted only of stearyl alcohol was supplied to plants to measure the effect of improving the vitality of plants. As a result, although a certain effect was observed, a large effect was not observed.

Comparative Example 3

A 2 L mixer (HIGH SPEED MIXER UM2E Model, manufactured by Mitsui Miike Engineering) was charged with 200 g of porous dextrin (Pineflow, manufactured by Matsutani Chemical Industry Co., Ltd.), to which were then added dropwise a mixture of 36 g of stearyl alcohol (Kalcol 8098, manufactured by Kao Corporation) and 108 g of polyoxyethylene sorbitan monolaurate (Reodol TW L-106, manufactured by Kao Corporation) which were melted and mixed at 70° C. in advance, followed by mixing with stirring to obtain a powdery plant vitalizer in which a primary alcohol and a surfactant which was a liquid at normal temperature were adsorbed to dextrin and which had an oil content of 10%.

The resulting powdery plant vitalizer had an average particle diameter of 110 μm. When added to water, it was dissolved and dispersed to form an emulsion-dispersion solution having an average emulsion diameter of about 10 μm. When the aqueous solution was supplied to plants, it produced the effect of improving the vitality of plants. However, when a load was applied to this powder, a mixture of the component (A) and the surfactant which was a liquid at normal temperature oozed out.

Comparative Example 4

A composition containing no powdery plant vitalizer was obtained in the same composition and operation condition as in Example 8 except that the powdery plant vitalizer was replaced with dextrin (trade name: Pinedex #2, manufactured by Matsutani Chemical Industry Co., Ltd.).

Comparative Example 5

A composition containing no powdery plant vitalizer was obtained in the same composition and operation condition as in Example 9 except that the powdery plant vitalizer was replaced with dextrin (Pinedex #2, manufactured by Matsutani Chemical Industry Co., Ltd.).

Comparative Example 6

A composition containing no powdery plant vitalizer was obtained in the same composition and operation condition as in Example 10 except that the powdery plant vitalizer was replaced with dextrin (Pinedex #2, manufactured by Matsutani Chemical Industry Co., Ltd.).

Comparative Example 7

A composition containing no powdery plant vitalizer was obtained in the same composition and operation condition as in Example 11 except that the powdery plant vitalizer was replaced with dextrin (Pinedex #2, manufactured by Matsutani Chemical Industry Co., Ltd.).

Test Example

With regard to the powdery plant vitalizers obtained in Examples 1 to 7 and Comparative Examples 1 to 3, the particle diameter, emulsion-dispersion diameter, component ooze rate and the effect of improving the vitality of plants were measured according to the following methods. The results are shown in Table 1.

With regard to the powdery plant vitalizers obtained in Examples 8 to 12 and Comparative Examples 4 to 7, the effect of improving the vitality of plants was measured according to the following method. The results are shown in Table 2.

1) Particle Diameter and Emulsion-Dispersion Diameter

The median diameter of the particle was measured using a laser diffraction/scattering type grain distribution measuring instrument LA-920 (manufactured by Horiba Ltd.) as an average particle diameter or an average emulsion-dispersion diameter. As the dispersing solvent, ethanol was used when measuring the diameter of the plant vitalizer and water was used when the emulsion-dispersion diameter of the plant vitalizer was measured. Also, when the emulsion-dispersion diameter of the plant vitalizer was measured, a suspension solution in which the solution concentration of a powder was about 1% was prepared as pretreatment by dissolving and dispersing the particle under stirring to the extent that the particle is mixed in water by a spoon and further diluted to a predetermined concentration when measured. In the measurement, the stirring was carried out at a middle level (specifically, the fourth rank among seven ranks of the measuring instrument LA-920). After the suspension solution was added to adjust to the predetermined concentration, middle level-ultrasonic wave (specifically, the fourth rank among seven ranks of the measuring instrument LA-920) was applied for 1 minute to measure dispersion diameter. It is to be noted that the single monovalent alcohol was measured by a row-tap method. In the examples, smaller particles were measured using a laser diffraction/scattering type grain distribution measuring instrument and larger particles having a size of 100 µm or more were measured by a row-tap method. The same result can be obtained by any of the both methods.

2) Ooze Rate of the Component

A cylindrical cell having a diameter of 2.5 cm was filled with 2 g of the powdery plant vitalizer and the powder layer was sandwiched between circular filter papers disposed on the upper and lower sides of the powder layer. This cell was set to a compactor (manufactured by Sankyo Dengyo (K.K)) at normal temperature and a load of 50 kg/cm$^2$ was applied to the cell from the above for 5 minutes to measure the weight of the component (A) or liquid including the component (A) which oozed from the cell and spread through the filter papers, thereby calculating the ooze rate according to the following calculating equation.

Ooze rate(%)={Weight of the oozed component($A$)or liquid including the component($A$)[g]/Theoretical amount of the component($A$)or liquid in the powder[g]}×100

3) Effect of Improving the Vitality of Plants

Measuring method (1): in the case of the powdery plant vitalizer (Examples 1 to 7 and Comparative Examples 1 to 3)

The plant vitalizer was supplied to a young tomato plant by using the following method to measure its growth rate.

Kind: "Home Momotaro" (Takii Shubyo (K.K)).

Culture container: Cell tray for germination with 50 holes, Pot having a diameter of 14 cm for culturing.

Used culture soil: Takii seeding culture soil (N:P$_2$O$_5$:K$_2$O=480:750:345 (mg/L), pH:6.4, EC:0.96)

The seeds were scattered on the 50 hole-cell tray in the above condition, the young plant was implanted in a pot 2 weeks after germinated and the plant vitalizer was supplied to the soil at intervals of one week totally three times three days after the plant was implanted. At this time, the plant vitalizer was dissolved and dispersed in water such that the content of the monohydric alcohol which was a major component was 50 ppm and the solution containing the plant vitalizer was supplied in an amount of 100 mL per pot.

After the third supply was finished, the growth state (height, and each weight (means live weight) of the ground part and the underground part) of each plant and the SPAD value (SPAD502, manufactured by Minolta Camera Co., Ltd.) indicating the degree of greenness of a leaf were measured. The measured value which was an average of the values measured three times to compare each value as a relative value when the case (Comparative Example 1) of adding no plant vitalizer was defined as 100.

Measuring method (2): in the case of the powdery plant vitalizer composition (Examples 8 to 12 and Comparative Examples 4 to 7)

Tomato seeds "Momotaro" were scattered in a box and then implanted in a pot in a stage in which three leafs were developed. As the culture soil, Kureha gardening culture soil (Kureha Chemical Industry Co., Ltd., fertilizer components: N:P:K=0.4:1.9:0.6 (g)/1 kg of culture soil) was used and the number of repetitions was set to 10 individuals. Treatment was started three days after the implantation in a pot was started. In the treatment, a solution in which the powdery plant vitalizer composition was properly diluted such that the concentration of nitrogen in the processing solution was 30 ppm was watered in the soil in a processing amount of 100 mL/pot at intervals of 7 days totally five times. The amount (total of the ground part and underground part) of the plants to be produced was investigated on the sixth day after the plants were treated five times. Each value in the table was a relative value when the case (Comparative Example 4) of adding no plant vitalizer was added was defined as 100 to compare these values with each other.

TABLE 1

|  |  | Example |  |  |  |  |  |  | Comparative example |  |  |
|---|---|---|---|---|---|---|---|---|---|---|---|
|  |  | 1 | 2 | 3 | 4 | 5 | 6 | 7 | 1 | 2 | 3 |
| Powdery plant vitalizer composition (% by weight) | Stearyl alcohol | 30.3 | 34.6 | 40.7 | 20.0 | 20.2 | 50.2 | 20.2 | Non-added (control) | 100.0 | 10.0 |
|  | Sodium caseinate |  |  |  | 19.0 | 19.3 | 12.0 | 14.6 |  |  |  |
|  | Emalstar #30A | 28.3 | 63.0 | 38.1 |  |  |  |  |  |  |  |
|  | DK-ester F-160 |  |  |  |  |  |  | 5.0 |  |  |  |
|  | Dextrin | 38.4 |  | 19.3 | 59.0 | 57.5 | 35.8 | 57.7 |  |  | 59.0 |
|  | Reodol TWL-106 |  |  |  |  |  |  |  |  |  | 30.0 |
|  | Water | 3.0 | 2.4 | 1.9 | 2.0 | 3.0 | 2.0 | 2.5 |  |  | 1.0 |
|  | Total | 100.0 | 100.0 | 100.0 | 100.0 | 100.0 | 100.0 | 100.0 |  | 100.0 | 100.0 |
| Average particle diameter (μm)*1 |  | 230 | 146 | 217 | 25 | 31 | 35 | 13 |  | 1000 | 110 |
| Average emulsion-dispersion diameter (μm)*2 |  | 0.5 | 1.3 | 7.7 | 3 | 0.9 | 0.4 | 2.5 | — | — | (10)*5 |
| Ooze rate (%)*3 |  | 0 | 0 | 0 | 0 | 0 | 0 | 0 |  | 0 | Unmeasurable (a large amount) |
| Plant vitality-improving effect*4 (relative value) | Height | 116 | 113 | 115 | 122 | 114 | 110 | 112 | 100 | 105 | 113 |
|  | Weight of underground part | 139 | 137 | 139 | 153 | 132 | 130 | 133 | 100 | 110 | 135 |
|  | Weight of ground part | 135 | 132 | 134 | 147 | 128 | 122 | 126 | 100 | 108 | 128 |
|  | SPAD value | 119 | 116 | 118 | 121 | 115 | 112 | 115 | 100 | 105 | 115 |

Note in Table 1)
*1 Average particle diameter of the powdery plant vitalizer.
*2 Average emulsion-dispersion diameter when the powdery plant vitalizer is dissolved and dispersed in water.
*3 Ooze rate from the powdery plant vitalizer.
*4 Measured by the measuring method (1)
*5 Solubilized state, liquid crystal state

TABLE 2

|  |  | Example |  |  |  |  | Comparative example |  |  |  |
|---|---|---|---|---|---|---|---|---|---|---|
|  |  | 8 | 9 | 10 | 11 | 12 | 4 | 5 | 6 | 7 |
| Powdery plant vitalizer composition (% by weight) | Powdery plant vitalizer | Same as in example 1 30.0 | Same as in example 1 40.0 | Same as in example 1 20.0 | Same as in example 1 40.0 | Same as in example 1 20.0 | Non-added (control) | Non-added | Non-added | Non-added |
|  | Fertilizer OKF2 | 63.0 | 55.0 | 37.5 |  | 37.5 | 63.0 | 55.0 | 37.5 |  |
|  | Fertilizer OKF17 |  |  |  | 35.0 |  |  |  |  | 35.0 |
|  | EDTA4Na | 5.0 |  |  |  |  | 5.0 |  |  |  |
|  | 3Na citrate |  | 4.0 | 2.5 |  | 2.5 |  | 4.0 | 2.5 |  |
|  | Succinic acid |  |  |  | 4.0 |  |  |  |  | 4.0 |
|  | Demol N | 2.0 | 0.5 | 0.5 |  | 0.5 | 2.0 | 0.5 | 0.5 |  |
|  | Emal 10P |  | 0.5 | 0.5 | 2.0 | 0.5 |  | 0.5 | 0.5 | 2.0 |
|  | Dextrin |  |  | 39.0 | 19.0 | 39.0 | 30.0 | 40.0 | 59.0 | 59.0 |
|  | Total | 100.0 | 100.0 | 100.0 | 100.0 | 100.0 | 100.0 | 100.0 | 100.0 | 100.0 |
| Plant vitality-improvement effect*1 (relative value) | Weight of underground part | 125 | 130 | 128 | 122 | 127 | 100 | 100 | 101 | 102 |
|  | Weight of ground part | 116 | 121 | 119 | 115 | 120 | 100 | 101 | 99 | 100 |

The invention claimed is:

1. A method of producing a powdery plant vitalizer, comprising the steps of preparing an O/W emulsion comprising a compound (A) that is $CH_3(CH_2)_{o-1}OH$ wherein o is an integer of 16 to 24, an emulsifying-dispersing agent (B), a water-soluble sugar (C) and water and drying the obtained emulsion by spraying;
the vitalizer having a structure in which the compound (A) is dispersed in the solid state in the form of an oil droplet having an average particle diameter of 0.4 to 7.7 μm.

2. The method as claimed in claim 1, in which the O/W emulsion is obtained from the compound (A) and a water-soluble sugar (C') having an emulsifying and/or dispersing function.

3. The method according to claim 1, wherein o of the compound (A) is an integer of 16-22.

4. The method according to claim 1, wherein o of the compound (A) is an integer of 16-22.

5. The method according to claim 1, wherein the vitalizer has an average emulsion-dispersion diameter of 2.5 to 7.7 μm.

* * * * *